(12) United States Patent
Rooks

(10) Patent No.: US 10,716,623 B2
(45) Date of Patent: Jul. 21, 2020

(54) BRONCHOSCOPE COUPLER

(71) Applicant: COVIDIEN LP, Mansfield, MA (US)

(72) Inventor: Kathy E. Rooks, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 564 days.

(21) Appl. No.: 15/491,032

(22) Filed: Apr. 19, 2017

(65) Prior Publication Data
US 2017/0319050 A1     Nov. 9, 2017

Related U.S. Application Data (60) Provisional application No. 62/332,097, filed on May 5, 2016.

(51) Int. Cl.
| | | |
|---|---|---|
| *A61B 1/00* | (2006.01) | |
| *A61B 90/57* | (2016.01) | |
| *A61B 18/18* | (2006.01) | |
| *A61B 18/00* | (2006.01) | |

(52) U.S. Cl.
CPC ........ *A61B 18/1815* (2013.01); *A61B 1/0014* (2013.01); *A61B 1/00128* (2013.01); *A61B 1/00147* (2013.01); *A61B 1/00149* (2013.01); *A61B 90/57* (2016.02); *A61B 2018/00541* (2013.01); *A61B 2018/00982* (2013.01); *A61B 2018/1861* (2013.01)

(58) Field of Classification Search
CPC ............ A61B 1/00112; A61B 1/00147; A61B 1/00149; A61B 1/0014; A61B 1/00121; A61B 90/57; A61B 90/50; A61B 2090/571; A61B 2034/305; F16B 2/10; F16B 2/185

USPC .......................................................... 600/102
See application file for complete search history.

(56) References Cited

U.S. PATENT DOCUMENTS

| | | | |
|---|---|---|---|
| 3,858,578 A | | 1/1975 | Milo |
| 4,573,452 A | | 3/1986 | Greenberg |
| 4,617,916 A | | 10/1986 | LeVahn et al. |
| 4,863,133 A | | 9/1989 | Bonnell |
| 4,867,404 A | | 9/1989 | Harrington et al. |
| 5,020,195 A | * | 6/1991 | LeVahn .................. A61B 17/02 24/514 |
| 5,447,149 A | | 9/1995 | Kikawada et al. |
| 6,834,837 B2 | | 12/2004 | Schilt et al. |
| 9,532,771 B2 | | 1/2017 | Ferzli |
| 9,610,135 B2 | * | 4/2017 | Nawrat .................. A61B 90/50 |
| 9,951,904 B2 | * | 4/2018 | Perez .................. F16M 13/022 |
| 2003/0225422 A1 | * | 12/2003 | Mosnier ............. A61B 17/2812 606/151 |

(Continued)

*Primary Examiner* — John P Leubecker (57) ABSTRACT

A coupling mechanism includes a base and a lever. The base is configured to couple to an external fixture. The lever is pivotably coupled to the base and transitionable between a clamped configuration and an unclamped configuration. A first pair of opposed arms extends from the base and a second pair of opposed arms extends from the lever in opposed relation to the first pair of opposed arms. In the clamped configuration the second pair of opposed arms are proximate the first pair of opposed arms, and in the unclamped configuration the second pair of opposed arms are spaced apart from the first pair of opposed arms. At least one of the first pair of opposed arms or the second pair of opposed arms includes a step thereon. The step is configured to receive and retain a surgical tool therein in the clamped configuration.

12 Claims, 11 Drawing Sheets

(56) References Cited

U.S. PATENT DOCUMENTS

| | | | |
|---|---|---|---|
| 2004/0267089 A1* | 12/2004 | Otsuka | A61B 1/00149 600/102 |
| 2006/0161136 A1* | 7/2006 | Anderson | A61B 90/57 606/1 |
| 2007/0185376 A1* | 8/2007 | Wilson | A61B 17/02 600/102 |
| 2010/0230567 A1* | 9/2010 | Schuerch | A61G 13/101 248/231.41 |
| 2012/0020929 A1 | 1/2012 | Macklis et al. | |
| 2015/0073407 A1* | 3/2015 | Dickhans | A61B 1/00133 606/41 |
| 2015/0351613 A1 | 12/2015 | Knight et al. | |
| 2016/0296401 A1* | 10/2016 | Cole | A61G 13/101 |
| 2017/0296297 A1* | 10/2017 | Zulty | A61B 17/12 |

* cited by examiner

BRONCHOSCOPE COUPLER

CROSS REFERENCE TO RELATED APPLICATION

The present application claims the benefit of and priority to U.S. Provisional Application Ser. No. 62/332,097, filed on May 5, 2016, the entire contents of which are incorporated herein by reference.

BACKGROUND

Technical Field

The present disclosure relates to bronchoscopy and, more specifically, to couplers for connecting and securing a bronchoscope to an external fixture.

Description of Related Art

A common interventional procedure in the field of pulmonary medicine is bronchoscopy, in which a bronchoscope is inserted into the airways through the patient's nose or mouth. Bronchoscopes are routinely used in the diagnosis and treatment of lung conditions, such as, lung cancer, airway stenosis, emphysema, etc.

The structure of a bronchoscope generally includes a long, thin, flexible tube that typically contains a lumen or working channel therethrough for the insertion of instruments therein, such as, diagnostic (e.g., biopsy tools, etc.) or therapeutic (e.g., laser, cryogenic, radio frequency, microwave tissue treatment probes, etc.) tools. Rotating a lever on the handle of the bronchoscope actuates a steering mechanism that deflects the tip in one or more directions such that the distal tip of the bronchoscope may be maneuvered and brought into approximation to target tissue.

During a typical procedure, the physician holds the bronchoscope handle with one hand and the bronchoscope tube with the other hand, and manipulates the distal tip of the bronchoscope inside the lung by rotating the deflection lever and by pushing and pulling the flexible tube of the bronchoscope. Once the distal tip is directed to target tissue, an instrument may be inserted into the working channel of the bronchoscope to perform a diagnostic or therapeutic procedure. In some situations an extendable working channel (EWC) is inserted into and through the working channel of the bronchoscope. The EWC defines a smaller diameter permitting access to more remote areas of the lung, and a working channel or lumen therethrough for the passage of instruments therein.

Certain challenges arise during such a procedure, such as, maintaining the distal tip of the bronchoscope or EWC at the target tissue during the procedure; the difficulty of simultaneously inserting the instrument into the working channel of the bronchoscope while holding the bronchoscope; the fatigue associated with holding the bronchoscope in a fixed position over long procedures; the potential for inadvertent actuation of the instrument, or further articulation of the bronchoscope, during the procedure; the potential for frequent and prolonged exposure to imaging radiation (such as Fluoroscopy, CT, CBCT, etc.) or other harmful side effects resulting from a clinician's proximity to an instrument; and the necessity to independently fix and stabilize the instrument such that the clinician may move away from the instrument during certain procedures. One solution often employed is to utilize multiple people such that one person operates the actuation mechanism and the flexible tube of the bronchoscope and a second person is employed to insert the instrument and perform other related tasks. However, this adds the cost of additional personal, and the necessity to accommodate these additional persons within the operating theater.

Accordingly, it is desirable to develop a system, method, and apparatus for use with a bronchoscope which facilitates the use of the bronchoscope and associated instruments, by a single practitioner.

SUMMARY

Provided in accordance with the present disclosure is a coupling mechanism including a base, a lever, a first pair of opposed arms, a second pair of opposed arms, and a step. The base is configured to couple to an external fixture. The lever is pivotably coupled to the base and moveable between clamped and unclamped configurations. The first pair of opposed arms extend from the base. The second pair of opposed arms extend from the lever in opposed relation to the first pair of opposed arms. In the clamped configuration, the second pair of opposed arms are proximate the first pair of opposed arms. In the unclamped configuration, the second pair of opposed arms are spaced apart from the first pair of opposed arms. The step is formed on at least one of the first or second pair of opposed arms. In the clamped configuration the step is configured to receive and retain a surgical tool therein.

In an aspect of the present disclosure, the coupling mechanism includes a biasing element disposed between the lever and the base such that the lever is biased into the clamped configuration. In a further embodiment, the biasing element is at least partially disposed within the base.

In yet another embodiment, the coupling mechanism includes a cap partially disposed within the base, where the biasing element is partially enclosed by the cap. In another embodiment, the cap further includes a protrusion extending therefrom. The protrusion is in opposed relation to the lever such that in the unclamped configuration the lever depresses the protrusion and the biasing element partially enclosed within the cap.

In a further embodiment, at least one of the first pair of opposed arms or the second pair of opposed arms further define a seat. In the clamped configuration the seat is configured to receive and retain a portion of a surgical tool therein.

In yet another embodiment, the coupling mechanism includes a quick release pin pivotably coupling the base and the lever, such that the lever is releasably coupled to the base.

In yet a further aspect of the present disclosure, a coupling mechanism is provided which includes a base and an arm. The base includes a pair of fingers configured to retain a portion of a bronchoscope. The arm is pivotably coupled to the base and transitionable between a clamped configuration and an unclamped configuration. In the clamped configuration, an inner surface of the arm is aligned with an inner surface of the base. In the unclamped configuration, the inner surface of the arm is misaligned with the inner surface of the base.

In an embodiment, the coupling mechanism includes a biasing element coupled between the base and the arm such that the arm is biased into the clamped configuration.

In another aspect of the present disclosure, a method is disclosed including pivoting a lever of a coupling mechanism into an unclamped configuration such that a first pair of opposed arms of the lever pivot away from a second pair of opposed arms of a base of the coupling mechanism. Further, a portion of a bronchoscope is inserted between the first and second pair of opposed arms and in abutment with a step. The step is disposed on at least one of the first or second pair of opposed arms. The lever is pivoted into a clamped configuration such that the first pair of opposed arms pivot towards the second pair of opposed arms to secure the bronchoscope therebetween.

In an embodiment, a portion of the bronchoscope is positioned within a seat defined between at least one of the first or second pair of opposed arms such that the portion is retained there between.

In a further embodiment, the method further includes pivoting the lever of the coupling mechanism into the unclamped configuration, and removing the bronchoscope from the coupling mechanism.

In yet another embodiment, pivoting the lever into the unclamped configuration further includes overcoming a biasing element disposed between the lever and the base.

In an embodiment, pivoting the lever into the unclamped configuration further includes depressing a cap at least partially disposed within the base with a protrusion extending from the cap.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure is directed to devices, systems, and methods for connecting and securing a diagnostic or therapeutic tool, e.g., a bronchoscope, to an external fixture. As will be discussed below, a coupling mechanism of the external fixture may be utilized to secure the bronchoscope during a procedure. The coupling mechanism may be fixed to, and articulate about, an end of the external fixture, and define a receiving portion configured to receive a portion of the bronchoscope therein. With the bronchoscope disposed within, and retained by, the receiving portion of the coupling mechanism, the articulation controls of the bronchoscope and the position of the flexible tubing of the bronchoscope are independent from the clinician. Accordingly, the clinician is not required to hold the bronchoscope for the entirely of the procedure, and may step away from the bronchoscope as needed to freely move about the operating theater. The coupling mechanism may also maintain the bronchoscope in a variety of orientations, with respect to a patient, such that the clinician may position the bronchoscope in any beneficial orientation for a given procedure. It is also envisioned that the clinician may also more easily control additional or supplemental surgical tools in cooperation with the bronchoscope, as the clinician is free from holding and maintaining the controls of the bronchoscope.

Embodiments of the present disclosure are now described in detail with reference to the drawings in which like reference numerals designate identical or corresponding elements in each of the several views. As is understood in the art, the term "clinician" refers to a doctor, a physician, a nurse, a bronchoscopist, or any other care provider or support personnel. Further, as is understood in the art the term "proximal" refers to the portion of the device or component thereof that is closest to the clinician and the term "distal" refers to the portion of the device or component thereof that is furthest from the clinician.

Figure 1:
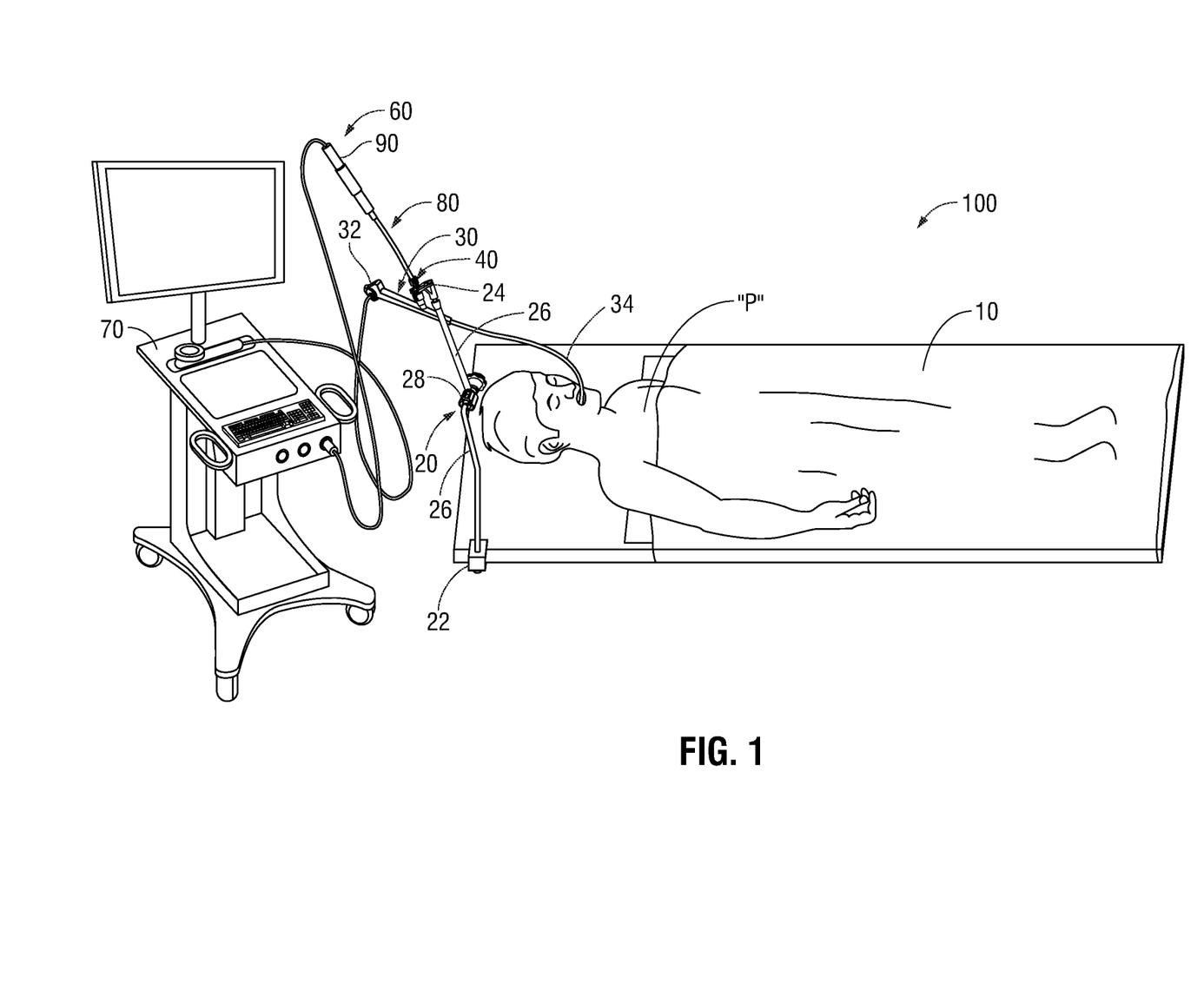
FIG. 1 is an illustration of a surgical system configured for use with a coupling mechanism in accordance with the present disclosure.
Figure 4A:
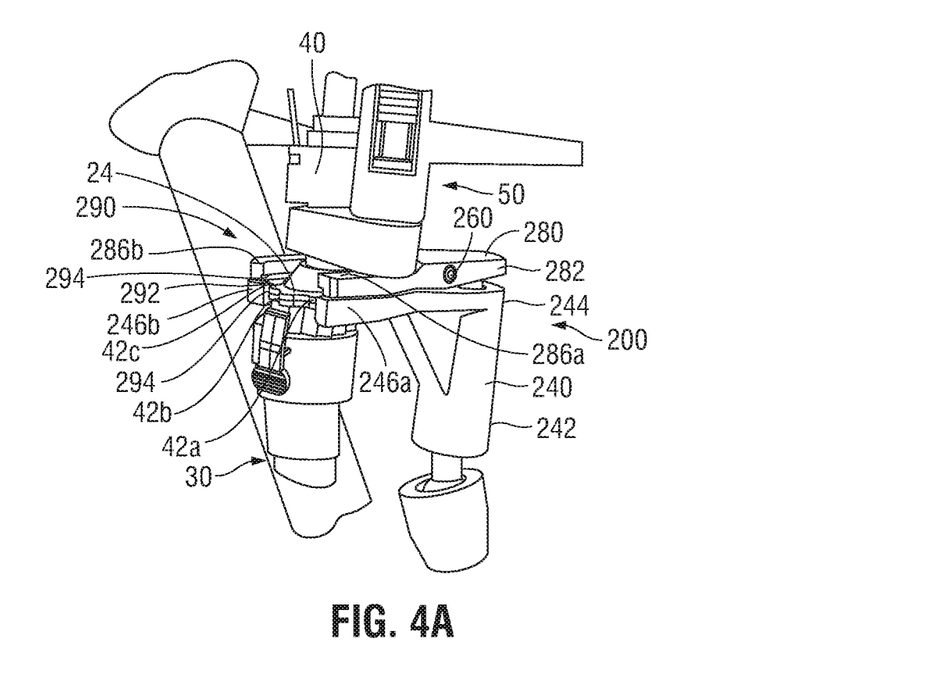
FIG. 4A is a front perspective view of the coupling mechanism of FIG. 2A coupled to the bronchoscope coupler of FIG. 3.
Figure 4B:
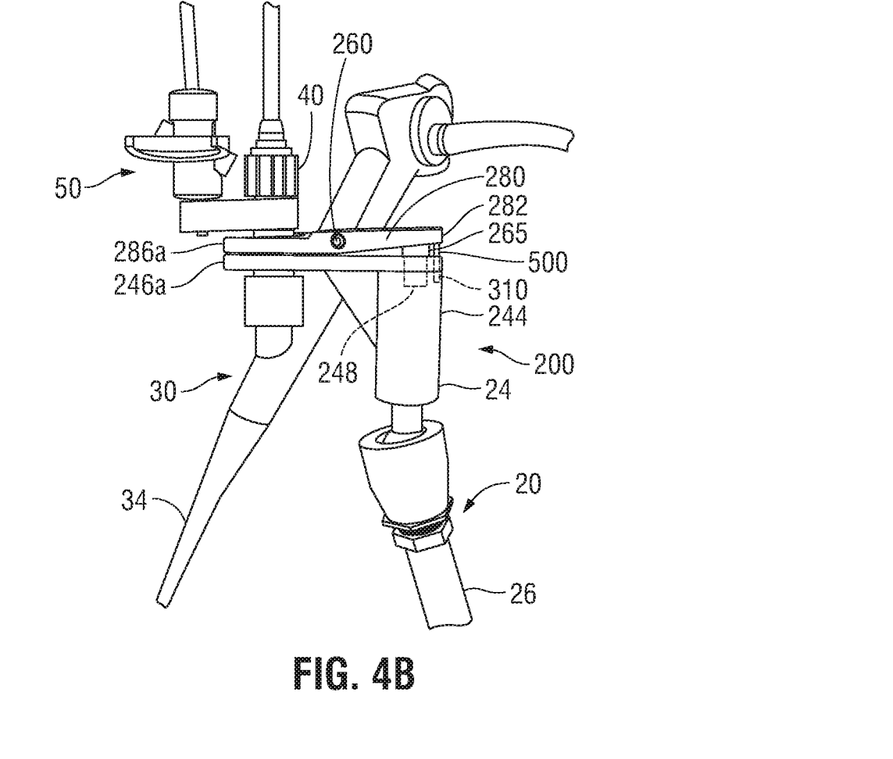
FIG. 4B is a side perspective view of FIG. 4A.

Referring now to FIG. 1, an exemplary bronchoscopic procedure 100 is illustrated which includes a procedure table 10, an external fixture 20, a bronchoscope 30, a bronchoscope adapter 40, a tool holder 50 (as illustrated in FIGS. 4A and 4B), and one or more surgical tools, i.e. diagnostic or therapeutic tools, 60 (e.g., a microwave ablation device). As is understood in the art, during a procedure a patient "P" is maintained on procedure table 10, permitting the clinician to insert the distal end (not explicitly shown) of the bronchoscope 30 into a natural opening or artificial incision of the patient. Through articulation of a control mechanism 32, and pushing or pulling of a flexible insertion tube 34 of the bronchoscope 30, the distal end of bronchoscope 30 may be directed and steered within the patient towards target tissue. Once the distal end of bronchoscope 30 is brought into proximity with target tissue, or alternatively can no longer traverse the patient's airway and following navigation of an extendable working channel to the target tissue, surgical tools 60 may be inserted through the bronchoscope 30.

It is envisioned that bronchoscopic procedure 100 may incorporate a microwave ablation catheter system which includes a microwave ablation generator 70, an extendable working channel (EWC) 80, and a microwave ablation device 90. The microwave ablation generator 70 is configured to provide microwave energy to the microwave ablation device 90. The EWC 80 is selectively insertable into and through the working channel of bronchoscope 30. The microwave ablation device 90 is configured to be selectively insertable into and through a working channel (not shown) of EWC 80. A proximal portion of EWC 80 extends proximally of bronchoscope adapter 40, where microwave ablation device 90 is insertable therein.

The EWC 80 may be first inserted into the working channel of bronchoscope 30. The microwave ablation device 90 may be inserted into the working channel of EWC 80. Utilizing the working channel of either the bronchoscope 30, or EWC 80, the microwave ablation device 90 is directed towards target tissue. As should be appreciated, it is desirable to keep the distal end of bronchoscope 30, and/or EWC 80, in proximity to target tissue during insertion and translation of microwave ablation device 90 therethrough.

In an exemplary procedure, the distal end of bronchoscope 30 is initially navigated through a patient's airway towards target tissue. Once the distal end of bronchoscope 30 is no longer capable of traversing through the airway of the patient (e.g., a dimension of bronchoscope 30 exceeds the airway), the EWC 80 may be utilized to extend the working channel of bronchoscope 30 to further navigate towards target tissue. EWC 80 is inserted through the working channel of bronchoscope 30 and translated distally such that the distal end of EWC 80 extends distally of the distal end of bronchoscope 30. With the distal end of the EWC 80 positioned in proximity to or in target tissue, microwave ablation device 90 may be inserted into the working channel of EWC 80 and brought into a desired position with respect to target tissue. Once the microwave ablation device 90 is localized with respect to target tissue, it is desirable to maintain the position of the microwave ablation device 90. As should be appreciated, clinicians may experience fatigue as a result of holding and controlling bronchoscope 30 throughout the procedure. The clinician is further burdened by the introduction and insertion of surgical tools 60. For example, EWC 80 and/or microwave ablation device 90 may add substantial weight to bronchoscope 30 making bronchoscope 30 unwieldy to hold and operate. As a result, surgical tools 60 (e.g., microwave ablation device 90) may be susceptible to movement (e.g., being pulled off target). Accordingly, external fixture 20 may be utilized to secure bronchoscope 30 to a fixed structure within the operating theater.

As illustrated in FIG. 1, external fixture 20 may be coupled to the procedure table 10. Generally, external fixture 20 may include a clamping mechanism 22, a coupling mechanism 24, and one or more arms 26 extending therebetween. A locking articulation joint 28 may couple each arm 26 to one another to permit selective articulation therebetween. It is envisioned that clamping mechanism 22 may be selectively coupled to any number of structures or assemblies within the operating theater, such that external fixture 20 is fixed with respect to a patient, such as, for example, procedure table 10, a surgical table, a robotic arm, a mobile cart, an overhead suspension system, etc. With external fixture 20 secured to an external structure within the operating/procedural theater, bronchoscope 30 may be coupled to coupling mechanism 24.

With reference to FIGS. 2A, 2B, 4A, and 4B, an embodiment of coupling mechanism 24 of external fixture 20 will be described with reference to coupling mechanism 200. Coupling mechanism 200 is configured to selectively receive and immobilize bronchoscope 30. Once clamped by the coupling mechanism 200, bronchoscope 30 is fixed with respect to external fixture 20, and bronchoscope 30 may be held in place independent of the clinician. Coupling mechanism 200 further serves to inhibit inadvertent articulation of control mechanism 32 of bronchoscope 30, longitudinal movement of flexible tube 34 of bronchoscope 30, and facilitates insertion, operation, and control of surgical tools 60 and/or EWC 80. Thus, coupling mechanism 200 reduces the difficulty and fatigue associated with the operation of bronchoscope 30.

Coupling mechanism 200 includes a base 240 and a lever 280. Base 240 includes a first end 242, a second end 244, and a pair of opposed arms 246a, 246b that extend from second end 244. First end 242 defines a mating recess 243 (shown in phantom in FIG. 2A) configured to couple base 240 to external fixture 20. Lever 280 includes a first portion 282 in opposed relation to second end 244 of base 240, and a pair of opposed arms 286a, 286b, where arms 246a, 246b are in opposed relation to arms 286a, 286b. Lever 280 is pivotably coupled to base 240 via pin 260. First portion 282 is tapered, or ramped, such that a gap "G" is defined between first portion 282 and second end 244 of base 240. Opposed arms 246a, 246b and 286a, 286b define an engagement interface 290. Engagement interface 290 has a generally "U" shaped, arcuate profile configured to receive and secure a portion of bronchoscope 30 therein. Alternatively, engagement interface 290 may define a patterned profile configured to correspond to the portion of the bronchoscope adapter 40.

Figure 2A:
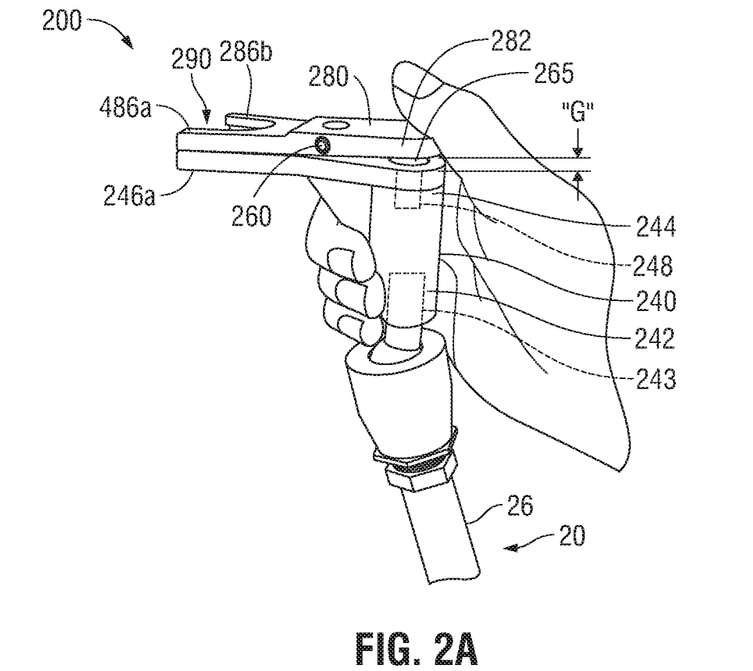
FIG. 2A is a side perspective view of an embodiment of the coupling mechanism in accordance with the present disclosure in a clamped configuration.
Figure 2B:
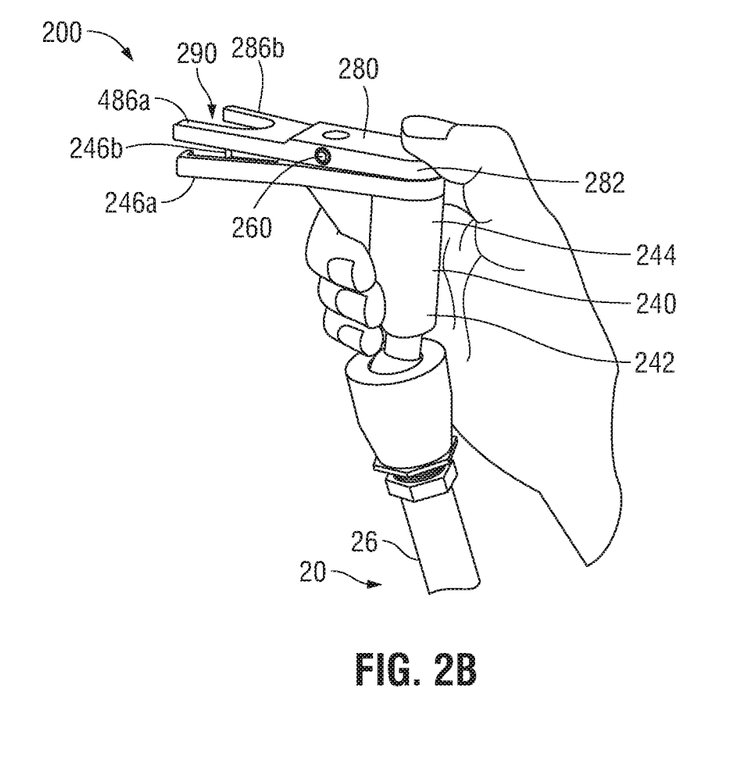
FIG. 2B is a side perspective view of the coupling mechanism of FIG. 2A in a unclamped configuration.

Lever 280 pivots about pin 260 between a clamped configuration (FIGS. 2A, 4A, and 4B) and an unclamped configuration (FIG. 2B). In the clamped configuration, engagement interface 290 engages and secures bronchoscope 30 thereto, thus coupling bronchoscope 30 and external fixture 20. In the unclamped configuration, bronchoscope 30 is releasable from engagement interface 290, and thus removable from coupling mechanism 200 and external fixture 20. It should be appreciated that the tapered, ramped feature of the first portion 282 of lever 280, and the gap "G" created thereby, permits lever 280 to transition between the clamped and unclamped configurations. Thus, in the clamped configuration arms 286a, 286b of lever 280 are in approximation with arms 246a, 246b of base 240, respectively, and in the unclamped configuration arms 286a, 286b are spaced away from arms 246a, 246b, respectively.

Figure 3:
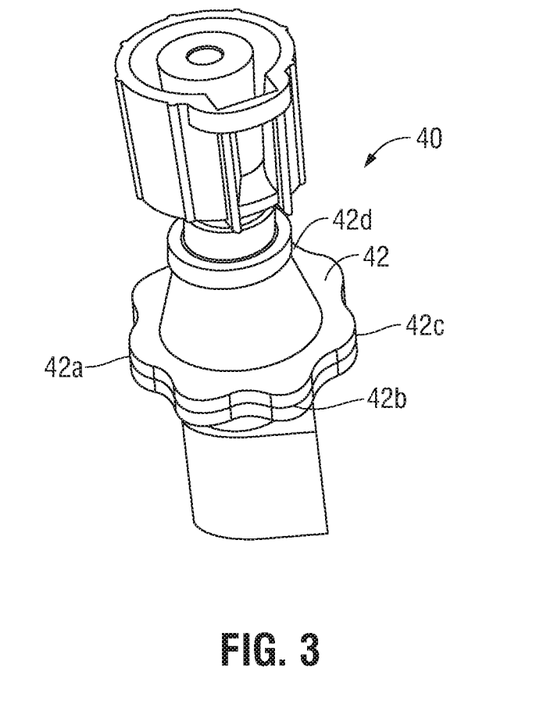
FIG. 3 is a front perspective view of an exemplary illustration of a bronchoscope adapter for use with the bronchoscope of FIG. 1.

More particularly, in the clamped configuration a portion of bronchoscope adapter 40 is positioned within, and clamped between, opposing arms 246a, 246b of base 240 and opposing arms 286a, 286b of lever 280. With brief reference to FIG. 3, an exemplary bronchoscope adapter 40 is illustrated. Bronchoscope adapter 40 includes a flange 42 having edges 42a-42d.

In the clamped configuration engagement interface 290 is configured to receive and retain the flange 42 therein, and clamp thereon (see FIGS. 4A and 4B). As illustrated in FIG. 4A, in the clamped configuration arm 246a of base 240 and arm 286a of lever 280 are in abutment with edge 42a of flange 40, and arm 246b of base 240 and arm 286b of lever 280 are in abutment with edge 42c. For further detail of bronchoscope adapter 40, reference is made to U.S. Patent Application Publication No. 2015/0351613, filed Mar. 20, 2015 and entitled "Bronchoscope Adapter", the entire contents of which is incorporated herein by reference.

Coupling and uncoupling of bronchoscope 30 and coupling mechanism 200 will now be described with reference to FIGS. 2A-4B. Initially, lever 280 is pivoted about pin 260 such that coupling mechanism 200 is transitioned into the unclamped configuration (FIG. 2B). With coupling mechanism 200 in the unclamped configuration, engagement interface 290 is positioned about bronchoscope adapter 40, such that arms 246a, 246b of base 240 and arms 286a, 286b of lever 280 are positioned about two opposing edges 42a, 42c or 42b, 42d of flange 42 of bronchoscope adapter 40. With flange 42 disposed within engagement interface 290, lever 280 is pivoted such that coupling mechanism 200 is transitioned into the clamped configuration (FIGS. 2A, 4A, and 4B). With coupling mechanism 200 in the clamped configuration, flange 42 is clamped between arms 246a, 286a and 246b, 286b of base 240 and lever 280, respectively, such that bronchoscope 30 is secured within coupling mechanism 200, and thus coupled to external fixture 20. Coupling mechanism 200 serves to fix bronchoscope 30 to external structure 20 such that bronchoscope 30 may be positioned in any desired orientation, such as, for example, with bronchoscope 30 in a vertical or horizontal relation with respect to patient "P". Coupling mechanism 200 additionally inhibits rotation of bronchoscope 30 about a longitudinal axis of bronchoscope 30, and further, facilitates rapid and secure fixation between bronchoscope 30 and external fixture 20.

As best illustrated in FIG. 4A, engagement interface 290 may further include a step 292 (e.g., a lip) and/or a seat 294 (e.g., a channel) disposed within or on arms 246a, 246b and/or arms 286a, 286b. Step 292 and seat 294 inhibit movement of bronchoscope adapter 40 out of the engagement interface 290. Step 292 is configured to abut, and thus capture, flange 42 within engagement interface 290, while seat 294 is configured to receive top or bottom surfaces of flange 42 therein. As illustrated in FIG. 4A, arms 246a, 246b include step 292, where arms 246a, 246b and 286a, 286b include seat 294, such that step 292 captures edge 42b and seat 294 receives the bottom surface of the flange 42. Accordingly, in the clamped configuration, seat 294 of arms 246a, 286a, and seat 294 of arms 246b, 286b, collectively act to define a recess to receive at least a portion of flange 42. As such, step 292 and seat 294 cooperatively act to inhibit bronchoscope 30 from sliding out of engagement interface 290. It should be appreciated that step 292 and seat 294 may be included on any combination of arms 246a, 246b, 286a, or 286b such that translation of bronchoscope 30 with respect to engagement interface 290 is inhibited.

Coupling mechanism 200 may include a biasing element 265 (FIGS. 2A and 4B) disposed between lever 280 and base 240, where biasing element 265 is disposed between the first portion 282 of lever 280 and second end 244 of base 240. Further still, a portion of biasing element 265 may be received within a cavity 248 of base 240 (shown in phantom in FIGS. 2A and 4B). Cavity 248 extends through at least a portion of base 240 from second end 244 towards first end 242. Biasing element 265 biases coupling mechanism 200 into the clamped configuration, such that as coupling mechanism 200 is transitioned into the unclamped configuration, i.e., lever 280 is pivoted about pin 260, the force provided by biasing element 198 is overcome.

Figure 5:
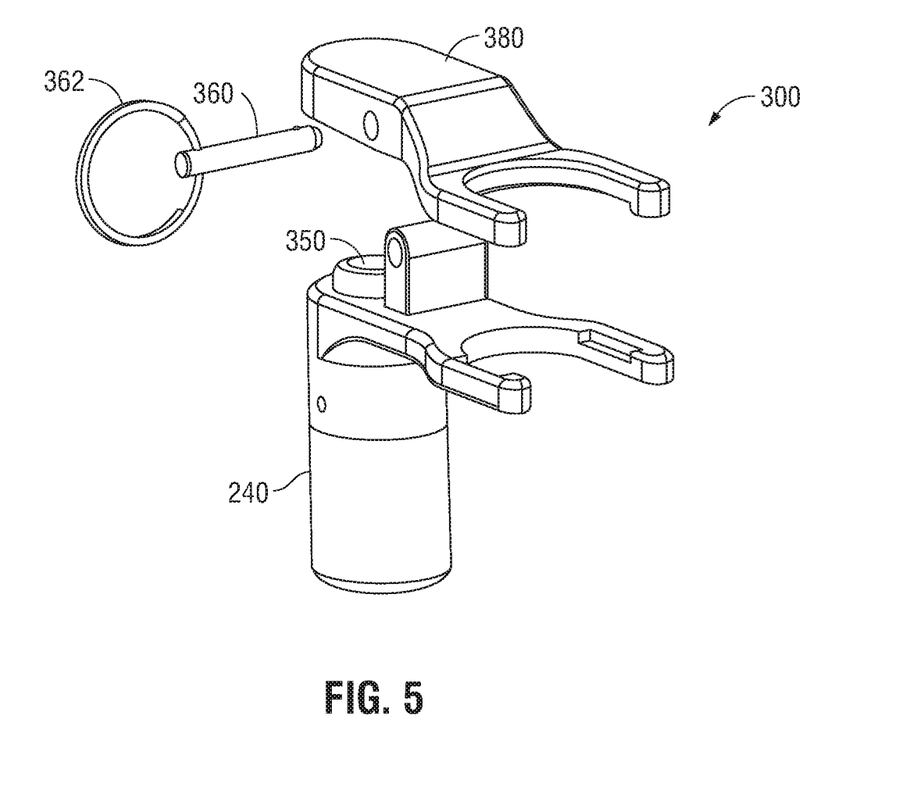
FIG. 5 is a front perspective view of another embodiment of a coupling mechanism in accordance with the present disclosure.
Figure 6A:
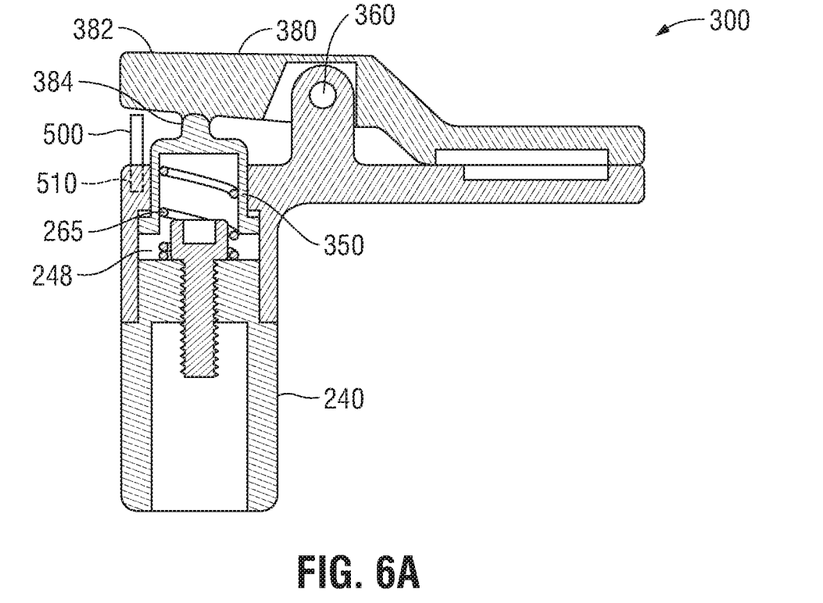
FIG. 6A is a cross-sectional view of the coupling mechanism of FIG. 5 in a clamped configuration.
Figure 6B:
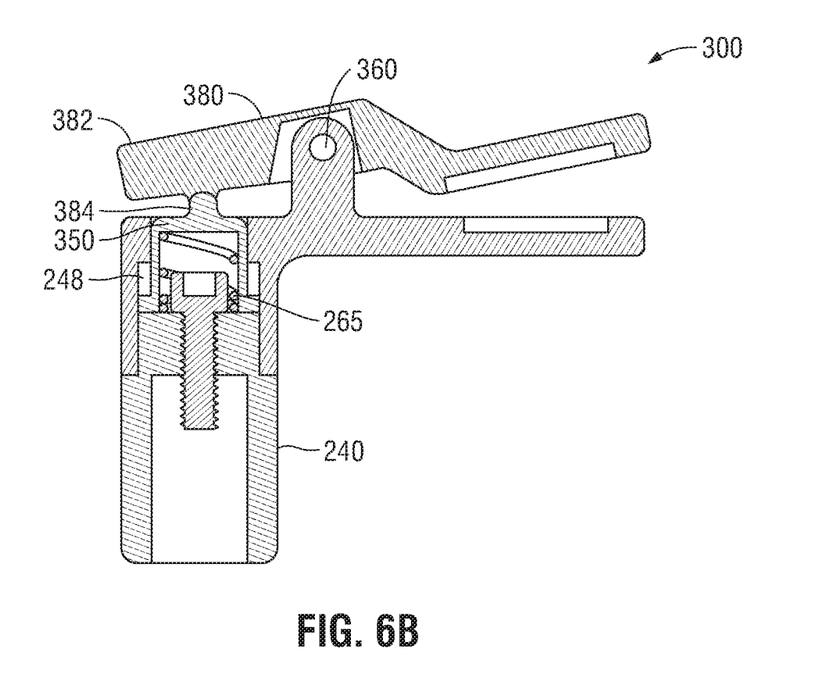
FIG. 6B is a cross-sectional view of the coupling mechanism of FIG. 5 in an unclamped configuration.

FIGS. 5-6B depict another embodiment of a coupling mechanism. The embodiments of FIGS. 5-6B include many similar features to those discussed above, and in the interest of brevity only differences and distinctions will be described herein.

A coupling mechanism 300 includes base 240, a lever 380, and a cap 350. Cap 350 is partially disposed within cavity 248 of base 240. Cap 350 is configured to enclose biasing element 265 therein to improved cleanability (FIGS. 6A and 6B). Cap 350 may further include a protrusion 384 disposed therebetween. As illustrated, protrusion 384 protrudes from an upper surface of cap 350 in opposed relation to a first portion 382 of lever 380. As coupling mechanism 300 transitions from the clamped configuration (FIG. 6A) to the unclamped configuration (FIG. 6B), protrusion 384 comes into contact with lever 380, thus cap 350 and biasing element 265 retained therein are depressed. It is envisioned that lever 380 may alternatively include a protrusion extend from a lower surface thereof, where the protrusion depresses cap 350 and biasing element 265 when coupling mechanism 300 is in the unclamped configuration.

Coupling mechanism 300 may include a quick release pin 360 removably received within base 240 and lever 380 such that lever 380 is releaseably coupled to base 240. Quick release pin 360 facilitates the cleaning and reprocessing of coupling mechanism 300, and further provides for emergency detachment of lever 380 from base 240, and thus bronchoscope 30 from coupling mechanism 300. It is further envisioned that quick release pin 360 may include a pull member 362 (FIG. 5) for expeditious removal and insertion. In an exemplary embodiment, pull member 362 is illustrated as a ring member, however it should be appreciated that any suitable ergonomic structure may be utilized to provide for easy and expeditious removal of quick release pin 360 from base 240 and lever 380. It should be appreciated that quick release pin 360 may be implemented with coupling mechanism 200 in a similar manner as described above.

Figure 7:
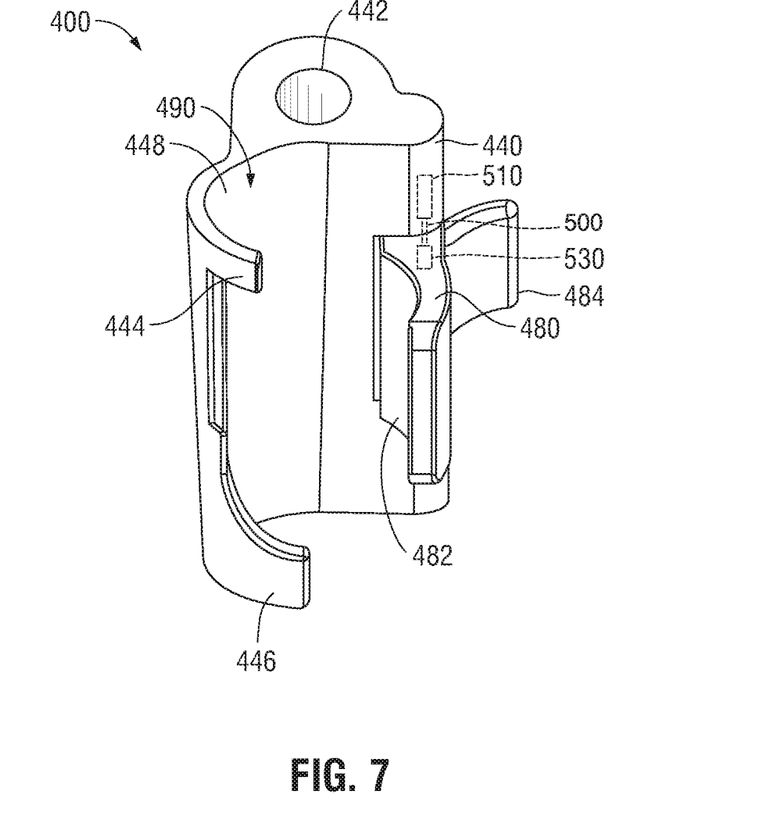
FIG. 7 is a front view of another embodiment of a coupling mechanism in accordance with the present disclosure.
Figure 8A:
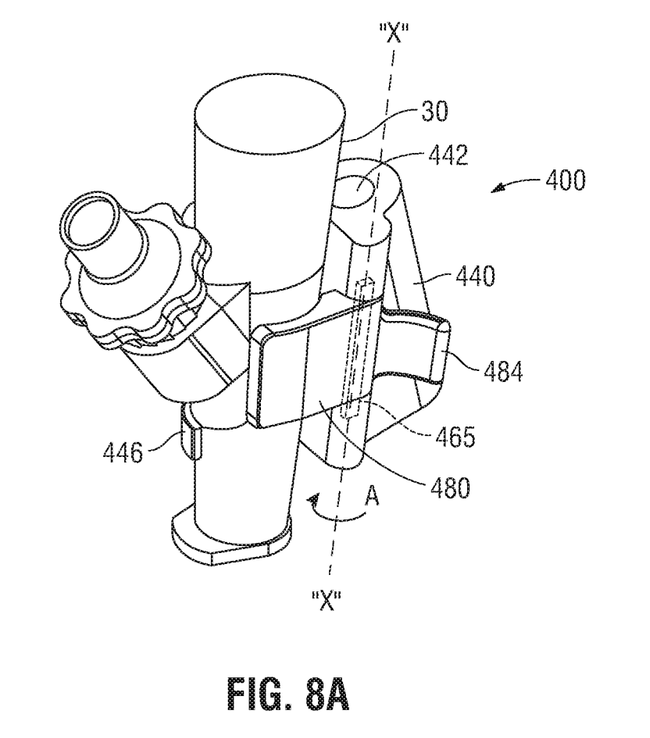
FIG. 8A is a front perspective view of the coupling mechanism of FIG. 7, in a clamped configuration, and coupled to a bronchoscope.
Figure 8B:
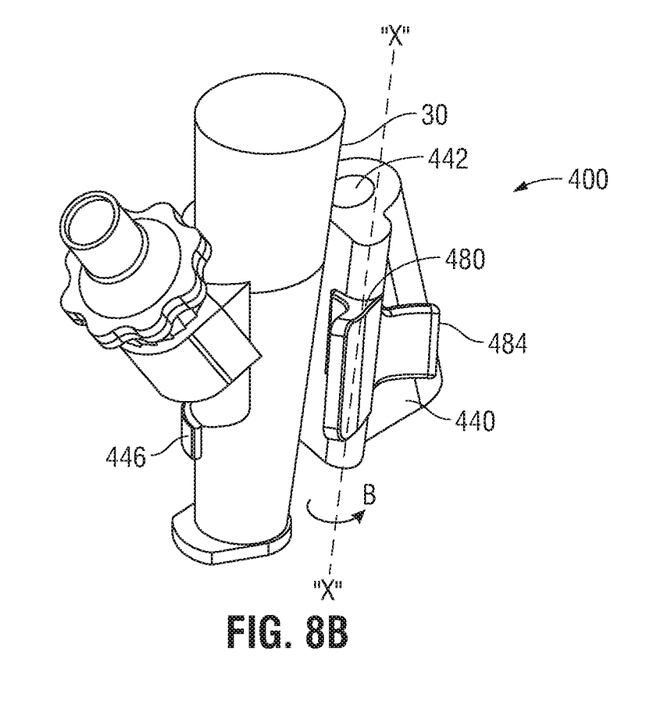
FIG. 8B is a front perspective view of the coupling mechanism of FIG. 8A, in a unclamped configuration.
Figure 9:
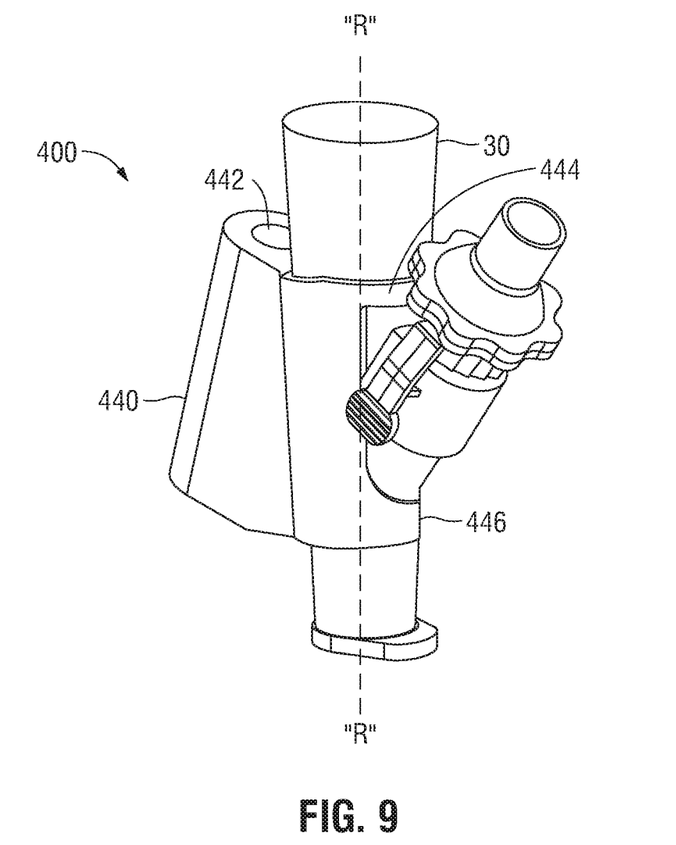
FIG. 9 is a side perspective view of the coupling mechanism of FIG. 8 coupled to a bronchoscope.

With reference to FIGS. 7-9 another embodiment of a coupling mechanism will be described. A coupling mechanism 400 includes a base 440, an arm 480 pivotably coupled thereto, and a receiving region 490 defined therebetween. Receiving region 490 is configured to receive a portion of bronchoscope 30 therein, and defines a generally arcuate profile configured to abut an outer surface of bronchoscope 30.

Base 440 defines a throughhole 442 configured to secure coupling mechanism 400 and external fixture 20. Base 440 further includes fingers 444 and 446 that are configured to engage a portion of bronchoscope 30. Fingers 444 and 446 serve to inhibit longitudinal translation of bronchoscope 30 along a longitudinal axis "R" of receiving region 490 (FIG. 9). Arm 480 is configured to pivot about axis "X" (FIGS. 8A and 8B) between a clamped configuration (FIG. 8A) and an unclamped configuration (FIG. 8B). In the clamped configuration, bronchoscope 30 is secured within receiving region 490, and in the unclamped configuration bronchoscope 30 is removable from receiving region 490. Arm 480 pivots in the direction of arrow "A" (FIG. 8A) into the clamped configuration. In the clamped configuration, an inner surface 482 of arm 480 aligns with, and forms a continuous surface with, an inner surface 448 of base 440 (FIG. 7). Arm 480 pivots in the direction of arrow "B" (FIG. 8B) into the unclamped configuration. In the unclamped configuration, inner surface 482 of arm 480 is brought out of alignment with inner surface 448 of base 440, thereby permitting removal of bronchoscope 30 therefrom.

Coupling mechanism 400 further includes a biasing member 465 (FIG. 8A) coupled between base 440 and arm 480. Biasing member 465 is configured to bias arm 480 into the clamped configuration. Arm 480 may include an ergonomic feature 484 configured to facilitate the transition of arm 480 between the clamped and unclamped configurations, such that coupling mechanism 400 may be easily and efficiently transitioned.

Further still, it is envisioned that any of coupling mechanisms 200, 300, or 400 may include a locking mechanism 500 configured to selectively inhibit inadvertent transition between the clamped and unclamped configurations. In such embodiments, inadvertent release of bronchoscope 30 from coupling mechanism 200, 300, and 400 may be prevented. Generally, locking mechanism 500 may be positioned between base 240 and lever 280 of coupling mechanism 200, or similarly positioned between base 240 and lever 380 of coupling mechanism 300, such that coupling mechanisms 200 and 300 are prevented from transitioning into the unclamped configuration. As illustrated in FIGS. 4B and 6A, locking mechanism 500 may be longitudinally slidable within cavity 510 (shown in phantom) defined in base 240 into and out of position between base 240 and lever 280, or lever 380. With reference to FIG. 7, locking mechanism 500 may be longitudinally translatable within cavity 510 (shown in phantom) defined in base 440 into an out of a corresponding cavity 530 (shown in phantom) defined in arm 480. With locking mechanism 500 positioned within both cavities 510 and 530, coupling mechanism 400 is prevented from transitioning into the unclamped configuration.

For the sake of brevity, and with reference to FIGS. 10A-11B, further embodiments of locking mechanism 500, locking mechanisms 500a and 500b, will be described with reference to coupling mechanism 300. However, it should be appreciated that coupling mechanism 200 or 400 may similarly incorporate the features described herein.

Figure 10A:
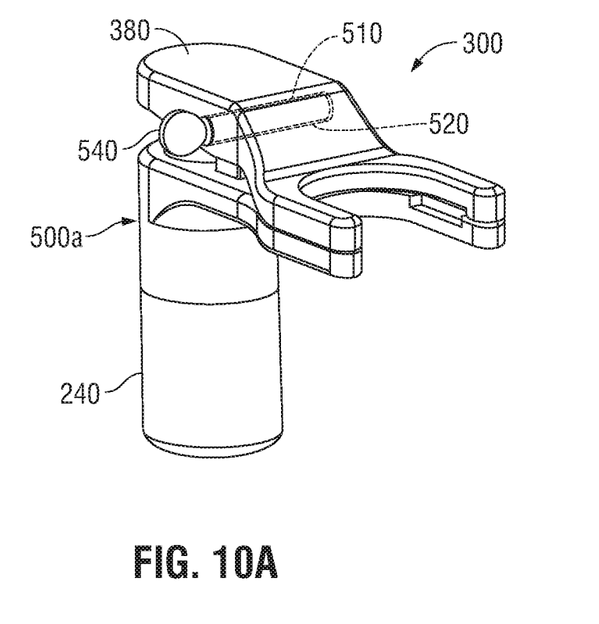
FIG. 10A is a side perspective view of the coupling mechanism of FIG. 5 with an embodiment of a locking mechanism.
Figure 10B:
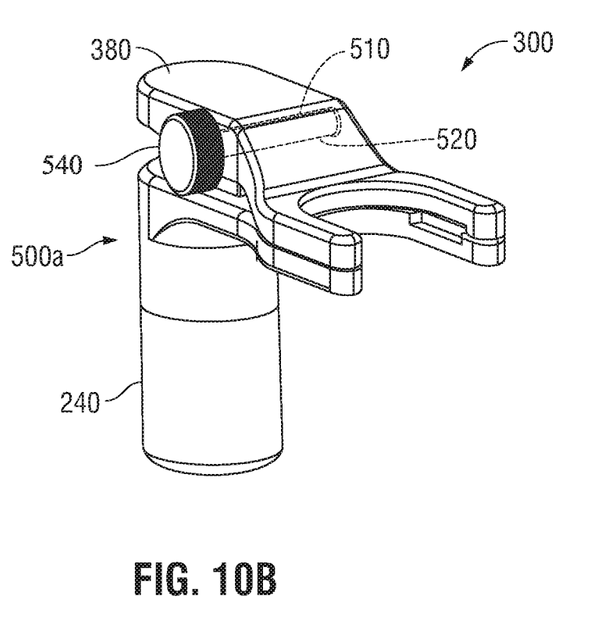
FIG. 10B is a side perspective view of another embodiment of the locking mechanism of FIG. 10A.

As illustrated in FIG. 10A, locking mechanism 500a includes a rotatable member 510 (illustrated in phantom) disposed within a pinhole 520 (illustrated in phantom) of base 240 and lever 380. It is envisioned that rotatable member 510 may be configured to, include a keying feature which engages a corresponding key locking feature disposed within pinhole 520; frictionally engages an inner surface of pinhole 520; and/or include a threaded portion along a portion thereof which engages a corresponding threaded engagement member (e.g., a nut, bolt, etc.) disposed within, or formed by, pinhole 520. Rotatable member 510 rotates in a first direction (e.g., clockwise) to lock coupling mechanism 300, where lever 380 is inhibited from pivoting into the unclamped configuration, and rotates in a second direction (e.g., counterclockwise) to unlock coupling mechanism 300, where lever 380 may freely pivot between the clamped and unclamped configurations. Rotatable member 510 includes a user engagement portion extending from at least one end of rotatable member 510, such as, for example, a flange portion 530 (FIG. 10A), a thumb screw 540 (FIG. 10B), or any other ergonomic feature known in the art. It is further envisioned that locking mechanism 500a may act in a similar manner as quick release pin 360, wherein locking mechanism 500a replaces quick release pin 360 such that locking mechanism 500a not only serves to lock coupling mechanism 300, but may be removed from pinhole 520 such that lever 380 may be uncoupled from base 240.

Figure 11A:
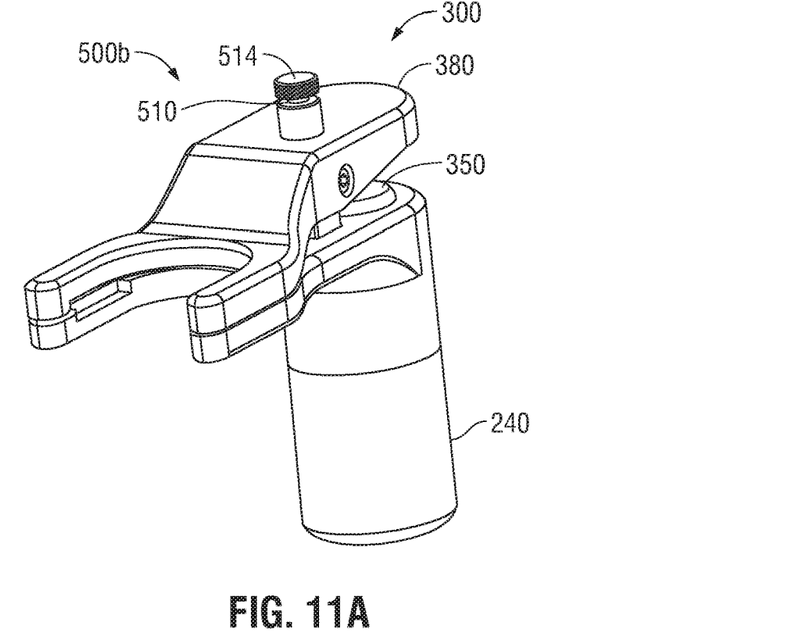
FIG. 11A is a side perspective view of the coupling mechanism of FIG. 5 with a further embodiment of a locking mechanism.
Figure 11B:
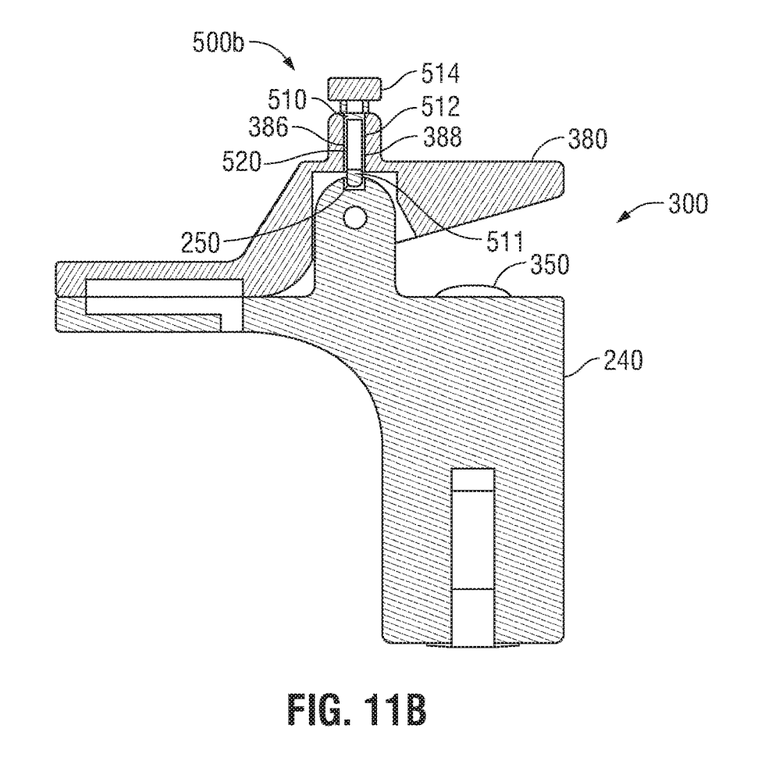
FIG. 11B is a cross-sectional view of the coupling mechanism and locking mechanism of FIG. 11A.

With reference to FIGS. 11A and 11B, locking mechanism 500b includes a retractable pin 510 having a threaded portion 512 and a user engagement portion 514. Pin 510 is disposed within a throughhole 386 of lever 380, and threaded portion 512 is configured to engage corresponding threads 388 of throughhole 386. Locking mechanism 500b may further include a biasing element 520 disposed within throughhole 386 and in communication with pin 510, such that pin 510 is spring loaded into one of a locked or unlocked position. Pin 510 slides between the locked position, wherein an end 511 of pin 510 is disposed within a recess 250 of base 240 (as illustrated in FIG. 11B), and an unlocked position where end 511 is removed from recess 250. As should be appreciated, with end 511 disposed within recess 250, lever 380 is inhibited from pivoting into the unclamped configuration.

In use, locking mechanism 500b may be slid against the bias of biasing element 520 such that end 511 is removed from recess 250. Locking mechanism 500b may than be rotated (e.g., clockwise or counterclockwise) such that threaded portion 512 engages threads 388, thus locking the position of end 511 outside recess 250. For ease of use, locking mechanism 500b may be configured such that approximately 90 degrees of clockwise or counterclockwise rotation engages and disengages the threaded portion 512 of pin 510 and the threads 388 of the throughhole 386. It is further envisioned that pin 510 may alternatively be positioned in juxtaposed relation to cap 350, or biasing element 265 disposed therein (FIGS. 6A and 6B), such that the pivoting of lever 380 from the clamped configuration to the unclamped configuration is similarly inhibited.

Bronchoscope 30 may be coupled to coupling mechanism 200, 300, or 400 at any point during a procedure. For example, bronchoscope 30 may be fixed to coupling mechanism 200, 300, or 400 prior to the insertion of bronchoscope 30 into patient "P"; during navigation of bronchoscope 30 within patient "P"; during insertion and translation of EWC 80; during insertion and/or actuation of surgical tools 60; or any combination thereof.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A coupling mechanism comprising:
a base configured to couple to an external fixture;
a lever pivotably coupled to the base and movable between a clamped configuration and an unclamped configuration;
a first pair of opposed arms extending from the base and having an inner peripheral surface defining a first opening configured to receive a portion of a surgical tool;
a second pair of opposed arms extending from the lever and in opposed relation to the first pair of opposed arms, the second pair of opposed arms having an inner peripheral surface defining a second opening configured to receive the portion of the surgical tool, in the clamped configuration the second pair of opposed arms are proximate the first pair of opposed arms and in the unclamped configuration the second pair of opposed arms are spaced apart from the first pair of opposed arms, wherein at least one arm of the first pair of opposed arms or the second pair of opposed arms has a cutout in the inner peripheral surface thereof, the cutout forming a bottom surface and a side surface each extending longitudinally along a length of the at least one arm, the bottom surface configured to resist longitudinal movement of the surgical tool and the side surface configured to resist lateral movement of the surgical tool, wherein the lever is configured to pivot relative to the base about a pivot axis that extends substantially perpendicular to a longitudinal axis of the surgical tool when the surgical tool is clamped between the first pair of opposed arms and the second pair of opposed arms.

2. The coupling mechanism of claim 1, further comprising a spring disposed between the lever and the base such that the lever is biased into the clamped configuration.

3. The coupling mechanism of claim 2, wherein the spring is at least partially disposed within the base.

4. The coupling mechanism of claim 2, further comprising a cap partially disposed within the base, the spring partially enclosed by the cap.

5. The coupling mechanism of claim 4, wherein the cap further includes a protrusion extending therefrom, the protrusion in opposed relation to the lever such that in the unclamped configuration the lever depresses the protrusion and the spring.

6. The coupling mechanism of claim 1, further comprising a quick release pin pivotably coupling the base and the lever, such that the lever is releasably coupled to the base.

7. The coupling mechanism according to claim 1, wherein the bottom surface and the side surface are perpendicular to one another, such that the cutout has an L-shaped transverse cross-sectional configuration.

8. A coupling mechanism comprising:
- an elongated base defining a longitudinally extending channel therethrough, the base including a pair of fingers longitudinally spaced from one another along a length of the base and defining a longitudinally-extending cavity therebetween configured to retain a portion of a bronchoscope;
- an arm having a first end pivotably coupled to the base, the arm configured to pivot relative to the base between a clamped configuration in which a curved inner surface of the arm is aligned with and forms a continuous surface with a curved inner surface of the base, and an unclamped configuration in which the inner surface of the arm is misaligned with the inner surface of the base; and
- a spring coupled between the base and the arm such that the arm is biased into the clamped configuration.

9. A method of performing a surgical procedure comprising:
- pivoting a lever of a coupling mechanism into an unclamped configuration such that a first pair of opposed arms of the lever pivot away from a second pair of opposed arms of a base of the coupling mechanism, the first pair of opposed arms having an inner peripheral surface defining a first opening and the second pair of opposed arms having an inner peripheral surface defining a second opening, at least one arm of the first pair of opposed arms or the second pair of opposed arms having a cutout in the inner peripheral surface thereof, the cutout forming a bottom surface and a side surface each extending longitudinally along a length of the at least one arm;
- inserting a portion of a bronchoscope into the first and second openings and in abutment with the bottom surface and the side surface; and
- pivoting the lever into a clamped configuration about a pivot axis such that the first pair of opposed arms pivot towards the second pair of opposed arms to secure the bronchoscope therebetween, the pivot axis being substantially perpendicular to a longitudinal axis of the bronchoscope when the bronchoscope is secured by the coupling mechanism.

10. The method of claim 9, further comprising:
- pivoting the lever of the coupling mechanism into the unclamped configuration; and
- removing the bronchoscope from the coupling mechanism.

11. The method of claim 9, wherein pivoting the lever into the unclamped configuration further includes overcoming a resilient bias of a spring disposed between the lever and the base.

12. The method of claim 9, wherein pivoting the lever into the unclamped configuration further includes depressing a cap at least partially disposed within the base with a protrusion extending from the cap.

\* \* \* \* \*